United States Patent [19]

Fry et al.

[11] 4,082,093
[45] Apr. 4, 1978

[54] COMPENSATOR VALVE

[75] Inventors: Stanley Eugene Fry; Claude Calvert Hurd, both of Riverside, Calif.

[73] Assignee: Bourns, Inc., Riverside, Calif.

[21] Appl. No.: 791,457

[22] Filed: Apr. 27, 1977

[51] Int. Cl.² ........................................... A61M 16/00
[52] U.S. Cl. ................................ 128/142.2; 128/145.8
[58] Field of Search ............... 128/145.8, 145.6, 145.5, 128/142.2, 203, 188, DIG. 17; 251/61.4, 61.5, 360; 137/DIG. 2, 625.5

[56] References Cited

U.S. PATENT DOCUMENTS

| | | | |
|---|---|---|---|
| 1,923,788 | 8/1933 | Mastenbrook | 137/625.5 |
| 3,231,232 | 1/1966 | Baumann | 251/61.4 |
| 3,874,629 | 4/1975 | Fontaine | 251/61.5 |
| 3,903,881 | 9/1975 | Weigl | 128/145.6 |

*Primary Examiner*—Robert W. Michell
*Assistant Examiner*—Henry J. Recla

*Attorney, Agent, or Firm*—Paul H. Ware; William G. Becker

[57] ABSTRACT

A compensator valve for use with a respirator/ventilator system having means for permitting patient assisted breathing and also permitting selection of a positive and expiratory pressure (PEEP). The system incorporating the advantages of the present invention generally incorporates an inhalation phase and an exhalation phase in its operative cycle. An exhalation valve assembly coupled into the system is operable between open and closed positions. This exhalation valve is maintained in a closed position during the time that breathing gas is being supplied to a patient. Operation of the compensator valve of the invention limits the exhalation/exhaustory pressure to a reference positive and expiratory pressure, thus affecting the patient's breathing effort. In practice, the difference between a reference positive and expiratory pressure and patient instantaneous exhaustory pressure causes the operation of the compensator valve of the invention so as to regulate the pressure applied to the exhaustion valve.

3 Claims, 2 Drawing Figures

COMPENSATOR VALVE

BACKGROUND OF THE INVENTION

1. Field of the Invention

This invention relates generally to artificial respiration systems and more particularly to control valves used in the implementation of such systems.

2. Description of the Prior Art

While presently available respiratory systems can furnish a volume of air to a patient's lungs, it is sometimes necessary to predetermine control parameters used to regulate the flow and pressure of breathing gas furnished. It has been found necessary in the operation of such expiratory apparatus to maintain an artificial residual pressure in the lungs under some conditions. This residual pressure may be called positive end expiratory pressure, and the parameter itself is so often used as to rate the acronym PEEP. Thus it is sometimes found necessary to hold a patient's lung pressure constant at the end of an expiratory cycle and through the start of an inspiratory cycle to this predetermined reference pressure, PEEP. Moreover, it is found in practice that the magnitude of the required PEEP may vary somewhat from inspiratory/expiratory cycle to cycle. Some disadvantages of the prior art respiratory systems include the lack of facility of variation of the PEEP after having it set at a particular average value. Thus a patient requiring a particular average value of PEEP over one inspiratory/expiratory cycle and having that value set up operating personnel is limited to that value until a new value is set up by operating personnel.

The basic types of prior art ventilators and respiratory devices are well-known. Many types have been developed and have been in clinical use for many years. Most of these prior art devices have met special needs as presented by specific problems and have thus served narrow purposes. Some of these prior art devices have been described in the following listed patents that were brought to the attention of the applicant through a novelty search conducted in the United States Patent and Trademark Office:

1. Ventilator and Method — U.S. Pat. No. 3,974,828 — Forrest M. Bird
2. Volume-Rate Respirator System and Method — U.S. Pat. No. 3,905,362 — Theodore B. Eyrick et al
3. Ventilator — U.S. Pat. No. 3,669,108 — Leif J. Sundblom et al
4. Therapeutic Intermittent Positive Pressure Respirator — U.S. Pat. No. 3,434,471 — Max D. Liston
5. Internally Actuated Combined Oxygen Pressure Regulator and Oxygen-Air Dilution Valves for Respiratory Apparatus — U.S. Pat. No. 3,386,458 — Lee S. Wasserman et al
6. Respiratory Apparatus — U.S. Pat. No. 3,339,545 — Geoffrey B. Burchell
7. Lung Ventilating Equipment — U.S. Pat. No. 3,307,542 — Christian B. Andreasen
8. Intermittent Positive Pressure Breathing Apparatus — U.S. Pat. No. 3,319,627 — Fred N. Windsor
9. Resuscitation Apparatus — U.S. Pat. No. 3,229,689 — Laurence Christman
10. Lung Ventilators and Timing Devices Therefor — U.S. Pat. No. 2,880,719 Christian B. Andreasen
11. Resuscitator — U.S. Pat. No. Re. 23,845 — Henry Seeler
12. Resuscitator — U.S. Pat. No. Re. 23,496 — Henry Seeler
13. Resuscitation Apparatus — U.S. Pat. No. 2,453,475 — Cornelius A. Tobias
14. Resuscitator Insufflator Aspirator — U.S. Pat. No. 2,408,136 — LeRoy G. Fox
15. Respiration Apparatus — U.S. Pat. No. 2,121,311 — Emil E. W. Anderson
16. Resuscitation and Artificial Respiration Apparatus — U.S. Pat. No. 1,848,232 — Robert B. Swope et al.

Many of these prior art systems and devices have had defects which have made them inappropriate and sometimes dangerous. Attention is drawn to the fact that none of these prior art devices attempts to regulate a positive end expiratory pressure on a cycle-to-cycle basis, so as to better serve the needs of a patient.

It would thus be a great advantage to the art to provide a system in which a PEEP is adjusted on a cycle-to-cycle basis so as to better serve a patient's cycle-to-cycle needs. It would be a concurrent advantage to provide such a system in a relatively inexpensive and uncomplicated form. A further desirable advantage would be to provide a means whereby existing artificial respiratory systems can be modified to afford adjustment of positive end expiratory pressures in the manner of the contemplation of the invention, in an economical and uncomplicated manner.

SUMMARY OF THE INVENTION

It is an object of the present invention to provide a system in which PEEP is regulated on a cycle-to-cycle basis.

It is a further object of the present invention to provide a system in which PEEP is regulated in part by the change in pressure resulting from the patient's own breathing needs during the course of spontaneous breaths.

It is a still further object of the present invention to provide means for modifying existing artificial respiratory systems so as to incorporate PEEP regulation on a cycle-to-cycle basis.

Still another object of the present invention is to provide such a system in an economical and convenient form.

In the accomplishment of these and other objects a compensator valve is provided whose main function is to hold the patient's lung pressure constant at the end of an expiration cycle and at the start of an inspiration cycle to a predetermined reference pressure. The apparatus of the invention includes a cover and a housing forming an enclosure. A valve and a disk generally make up a metering control of gas flow so as to maintain a constant pressure. The disk and a pin or shaft transfer forces from a diaphragm to a ball valve. The diaphragm is a thin, flexible member that senses patient pressure on one side and a predetermined reference pressure (PEEP) on the other. When patient pressure exceeds reference pressure, a force transmitted by the shaft unseats the ball and the ball valve, thus allowing gas to flow from an exhalation valve thus reducing the exhalation valve pressure. The reduction in exhalation valve pressure allows flow from the patient's circuit through the exhalation valve to continue until the patient pressure and the reference pressure are equal. Thus the patient's pressure is operative to participate in the control of the reference positive end expiratory pressure on a cycle-to-cycle basis.

BRIEF DESCRIPTION OF THE DRAWINGS

Further advantages and features of the present invention will be more fully apparent to those skilled in the art to which the invention pertains from the ensuing detailed description thereof, regarded in conjunction with the accompanying drawings wherein like reference characters refer to like parts throughout and in which.

DETAILED DESCRIPTION

Although specific embodiment of the invention will now be described with reference to the drawings, it should be understood that such embodiments are by way of example only and merely illustrative of but a small number of the many possible specific embodiments which can represent applications of the principles of the invention. Various changes and modifications obvious to one skilled in the art to which the invention pertains are deemed to be within the spirit, scope and contemplation of the invention as further defined in the appended claims.

Figure 1:
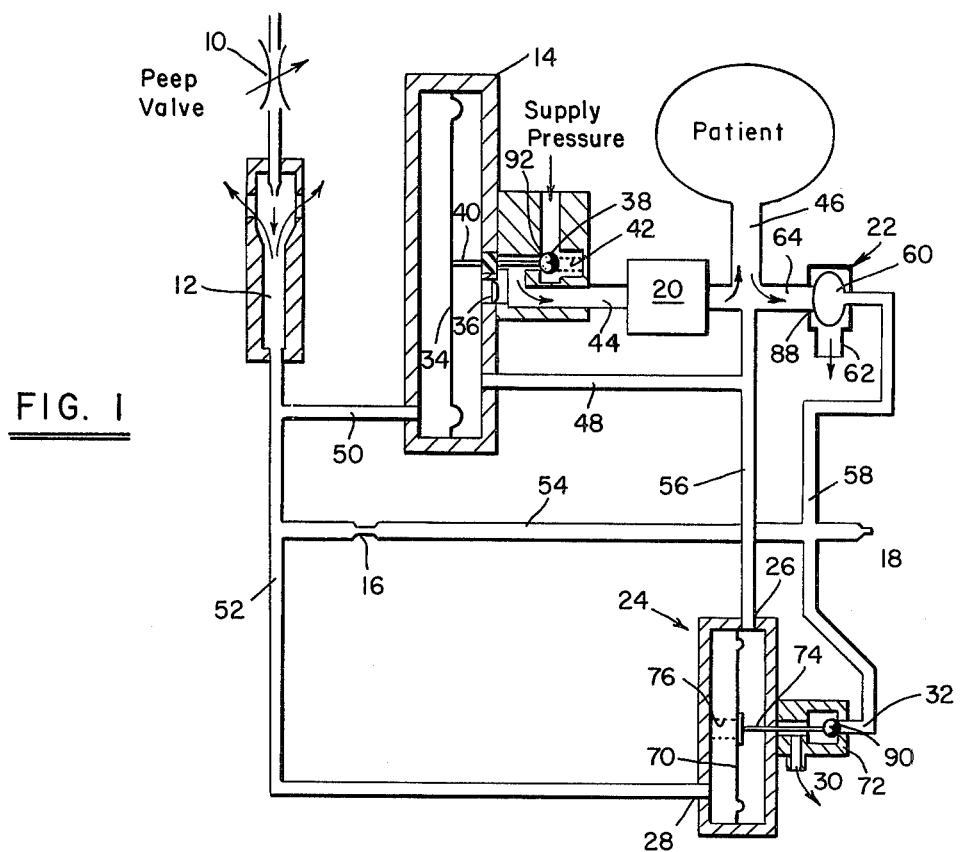
FIG. 1 is a schematic diagram illustrating the integration of the compensator valve into a conventional artificial respiratory system so as to gain the advantages of the invention.

Referring to FIG. 1 with greater particularity, the operation of the compensator valve of the invention in a typical artificial respiratory system may be examined. Upon inspection of FIG. 1, it will be seen that the system has been improved by the incorporation of the compensator valve which is the subject of this invention.

A positive end expiratory reference pressure is set up by the cooperative actions of the PEEP valve 10 and venturi 12. This reference pressure is incident at demand valve 14, reference orifice 16 and compensator valve 24 by means of conduit 52. Conduit 52 communicates with demand valve 14 by means of conduit 50 thus causing reference pressure to be incident upon the left-hand side of diaphragm 34. The patient's attempt to breathe is communicated to the right-hand side of diaphragm 34 by means of conduit 48 as a reduced pressure. This reduced pressure, incident at the right-hand side of diaphragm 34, causes that diaphragm to move to the right thus causing the shaft 40 to force ball 38 to unseat in opposition to the force of spring 42. When the ball 38 is unseated, supply pressure from an external source of breathing gas, not shown, is incident in conduit 44. The supply pressure is also incident upon check valve 36 and maintains that valve in a closed position. Patient circuit 20 receives the breathing gas from conduit 44 and delivers the breathing gas to the patient by means of conduit 46. The reduced pressure resulting from the patient's attempt to breathe is communicated to compensator valve 24 by means of conduit 56 at a port denoted by numeral 26. This pressure is incident upon diaphragm 70 at its right-hand side. The pressure at the left of diaphragm 70 is the reference pressure communicated thereto by the conduit 52 at a port denoted by numeral 28. Reduced pressure to the right of diaphragm 70 cooperating with reference pressure in conduit 52 and the force of spring 76 serves to move firmly seat ball 72 upon compensator valve seat 90. It will be noted that reference pressure in conduit 52 is incident at reference orifice 16 and thence by means of conduit 54 this reference pressure is transmitted to fixed bleed orifice 18. The reduced pressure resulting from the patient's attempt to breathe is additionally transmitted by means of conduit 64 to exhalation valve 22 where it causes exhalation valve balloon element 60 to seat more firmly against exhalation valve seat 88.

Upon patient's exhalation, a different set of circumstances obtains. An increased pressure is transmitted by means of conduit 48 to the right-hand side of diaphragm 34. In being urged to the left in response to this increased pressure, diaphragm 34 in cooperation with the force of spring 42 causes ball 38, which is connected to diaphragm 34 by shaft 40, to seat more firmly against demand valve seat 92 thus cutting off the supply pressure of the breathing gas. This same increased pressure, however, is also incident upon compensator valve diaphragm 70 at the right-hand side thereof by means of conduit 56 at port 26. This increased pressure causes the diaphragm 70 to move to the left thus permitting the ball 72 to unseat from its seat 90. At the same time, this increased pressure is transmitted by means of conduit 64 to exhalation valve 22 and is incident against exhalation valve balloon element 60 tending to collapse it. Since port 32 is open because of the action of diaphragm 70 in unseating ball 72 from its seat 90, pressure in exhalation valve balloon element 60 can exhaust to atmosphere through conduit 58 and port 30 of compensator valve 24. Upon the partial collapse of exhalation valve balloon element 60, it also becomes unseated from its seat 88 thus allowing the patient's exhalation to escape to atmosphere through port 62.

When the pressures on each side of compensator valve diaphragm 70 become equal, ball 72 will seat against seat 90 under the action of spring 76 acting through shaft 74. Exhalation valve balloon element 60 will become inflated by means of reference orifice 16 acting through conduits 54 and 58 to a pressure controlled partly by fixed bleed orifice 18. The inflation of exhalation valve balloon element will cause it to seat against seat 88 thus terminating the exhaust to atmosphere through port 62. It will thus be appreciated that the seating of the exhalation valve balloon element 60 is a function of the Positive End Expiratory reference Pressure (PEEP) and the patient's expiratory pressure.

Figure 2:
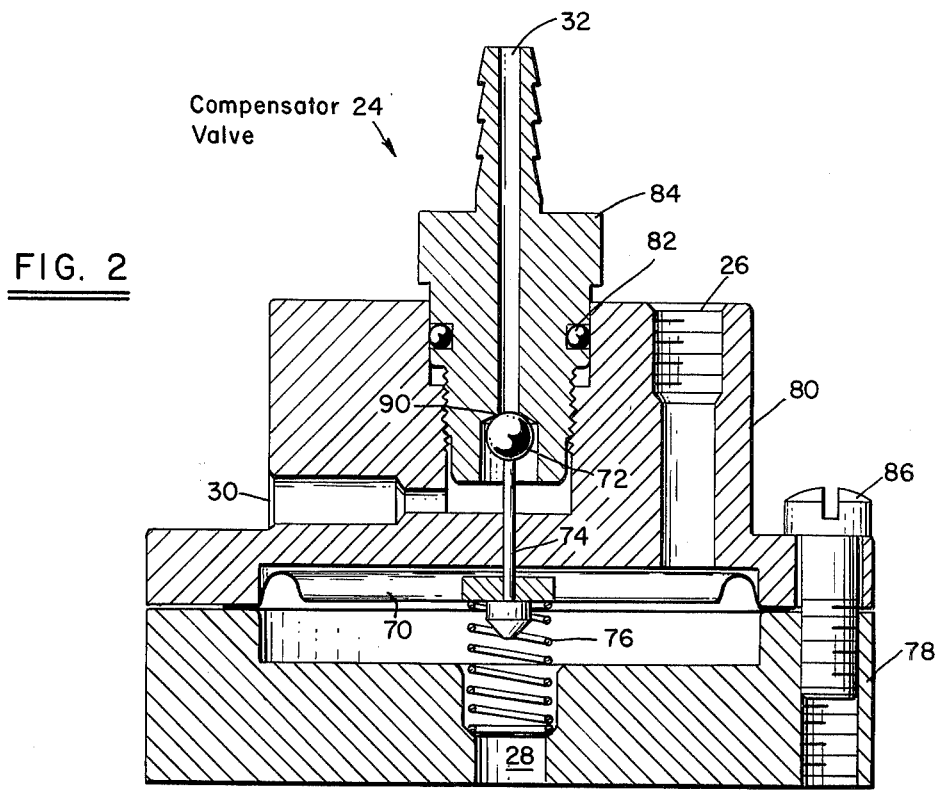
FIG. 2 is a detailed drawing of the compensator valve of the invention.

Referring now to FIG. 2, the compensator valve may be examined in greater detail apart from its integration into the artificial respiratory system. A screw 86, or some other means, is useful to secure housing 80 to the body 78 of the compensator valve 24 thus making the valve a differential pressure capsule. A port 32 is provided in adjustable valve fitting 84 which is screwed into housing 80 and sealed by O-ring seal 82. A port 26 is provided to communicate with the upper chamber of the compensator valve 24 while a port 28 communicates with the lower chamber thereof. A compression spring 76 urges the diaphragm 70 in an upward direction to compensate for forces encountered in adjusting and operating the compensator valve. A port 30 provides a bleed to atmosphere function necessary in the operation of the compensator valve as explained above. Ball valve 72 seats against compensator valve seat 90 and is connected to diaphragm 70 by shaft 74. It may be observed that adjustment of adjustable valve fitting 84 further into the housing 80 will cause ball 72 to seat more firmly against seat 90 because of the compression force of spring 76. The ratio of pressures in the upper and lower chambers or compensator valve 24 at which ball 72 will unseat from its seat 90 is thus adjustable over a small range by the action of adjustable valve fitting 84.

Thus there has been described a compensator valve for use with a respirator/ventilator system having means for permitting patient assisted breathing and also permitting selection of a reference positive end expiratory pressure in which a positive end expiratory pressure can be adjusted on a cycle-to-cycle basis during both spontaneous and positive pressure breaths. Great improvements in patient safety and comfort have thus been provided through the novel advantages of the invention.

It is pointed out that although the present invention has been shown and described with reference to particular embodiment, nevertheless various changes and modifications obvious to one skilled in the art to which the invention pertains are deemed to lie within the purview of the invention.

What is claimed and desired to be secured by Letters Patent of the United States is:

1. A respirator system connected to a source of breathing gas under pressure having an inspiratory phase and an expiratory phase in its operative cycle comprising:
    means for originating and maintaining a positive and expiratory pressure (PEEP);
    venturi assembly means responsive to the PEEP and having an output;
    demand valve means differentially responsive to the output pressure from said venturi assembly means and inspiratory/expiratory patient pressure to control the supply pressure of the breathing gas under pressure;
    patient circuit means responsive to the supply pressure as controlled by said demand valve means;
    exhalation valve means;
    reference orifice means responsive to output pressure from said venturi assembly means and supplying pressure to said exhalation valve means, said exhalation valve means being differentially responsive to patient expiratory pressure and said pressure from the reference means;
    fixed bleed orifice means responsive to output pressure from said reference orifice means;
    compensator valve means differentially responsive to pressure from said venturi assembly means and the expiratory pressure from a patient so as to operate said exhalation valve means and maintain the patient's expiratory pressure at the PEEP reference level.

2. The system of claim 1, wherein said compensator valve comprises:
    a valve housing attached to a body defining first pressure port means responsive to a patient's expiratory pressure;
    second pressure port means responsive to a positive and expiratory reference pressure;
    first pressure chamber means in fluid communication with said first pressure port means;
    second pressure chamber means in fluid communication with said second pressure port means;
    flexible resilient means for separating said first pressure chamber means from said second chamber means;
    an adjustable valve fitting in said valve housing having third pressure port means;
    a valve seat in said adjustable valve fitting at an interior end of said third pressure port;
    ball valve means for seating at said valve seat;
    a shaft linking said ball valve to said flexible resilient means;
    a spring operative to maintain a position of said flexible resilient means;
    fourth pressure port means in fluid communication with atmospheric pressure and said third pressure port means when said ball valve means is unseated from said valve seat.

3. In a ventilator for a patient including means for providing an inhalation phase and an exhalation phase in its operative system having patient connection means and pressure responsive exhalation valve means and including means for determining and providing a positive end expiratory reference pressure in respect to a patient user of said ventilator system with means for distribution of said positive end expiratory reference pressure within the system of the ventilator and first sensing means for sensing a pressure differential between an effort to breathe initiated by said patient user of said ventilator and said reference pressure, and means responsive to said first sensing means within the system of said ventilator for controlling a supply of breatheable gas to be furnished to the patient user of said ventilator and additionally providing second sensing means for sensing a pressure differential between an end expiratory lung pressure remaining in said patient user's lungs at the termination of an expiration and said reference pressure and for varying said patient user's end expiratory lung pressure during any exhalation phase as a function of said positive end expiratory reference pressure, said second sensing and varying means comprising:
    a valve housing;
    first pressure chamber means in said housing including a first pressure port means communicating with said patient connection means;
    second pressure chamber means also defined in said housing including a second pressure port means communicating with said distributing means;
    flexible resilient means located in said housing for separating said first pressure chamber means from said second chamber means and resiliently movable therebetween;
    an adjustable valve fitting mounted on said valve housing having a third pressure port means communicating with said exhalation valve means;
    a valve seat in said adjustable valve fitting communicating with said third pressure port;
    ball valve means in said adjustable valve fitting for seating at said valve seat;
    shaft means linking said ball valve to said flexible resilient means;
    spring means in said second pressure chamber operative to maintain positive bias upon said flexible resilient means so as to maintain said ball valve seated against said valve seat;
    fourth pressure port means in fluid communication with atmospheric pressure and said third pressure port means when said ball valve means is unseated from said valve seat thereby, varying the pressure in said pressure responsive exhalation valve means during any exhalation phase as a function of said positive end expiratory reference pressure.

* * * * *

UNITED STATES PATENT OFFICE
CERTIFICATE OF CORRECTION

Patent No. 4,082,093      Dated April 4, 1978

Inventor(s) Stanley Eugene Fry and Claude Calvert Hurd

It is certified that error appears in the above-identified patent and that said Letters Patent are hereby corrected as shown below:

In the Abstract, line 3, the second "and" should read -- end --

In the Abstract, line 13, "and" should read -- end --

In the Abstract, line 16, the first "and" should read -- end --

Column 1, line 31, insert -- by -- after "set up"

Column 3, line 65, "move" should read -- more --

Column 5, line 26, the second "and" should read -- end --

Column 5, line 58, "and" should read -- end --

Signed and Sealed this

Fifteenth Day of August 1978

[SEAL]

Attest:

RUTH C. MASON
*Attesting Officer*

DONALD W. BANNER
*Commissioner of Patents and Trademarks*